United States Patent [19]

Atlas

[11] Patent Number: 5,107,846
[45] Date of Patent: Apr. 28, 1992

[54] DISPLACEMENT DETECTOR DEVICE AND METHOD

[76] Inventor: Dan Atlas, Mishavim Street 20, Hod Hasharon, Israel

[21] Appl. No.: 573,752

[22] Filed: Aug. 28, 1990

[30] Foreign Application Priority Data

Aug. 31, 1989 [IL] Israel .................................. 91491

[51] Int. Cl.⁵ .............................................. A61B 5/08
[52] U.S. Cl. ........................................ 128/666; 128/671;
128/721; 128/782; 250/227.21; 356/373
[58] Field of Search ................ 356/41, 373; 128/665,
128/666, 667, 671, 675, 714, 721, 748, 774, 782;
73/705; 250/227.11, 227.21, 231.1, 231.11,
231.19

[56] References Cited

U.S. PATENT DOCUMENTS

| | | | |
|---|---|---|---|
| 3,789,667 | 2/1974 | Porter et al. | 73/705 |
| 4,472,022 | 9/1984 | Bearcroft et al. | 73/705 |
| 4,543,961 | 10/1985 | Brown | 128/667 |
| 4,611,600 | 9/1986 | Cohen | 128/667 |
| 4,712,566 | 12/1987 | Hök | 128/748 |
| 4,838,279 | 6/1989 | Fore | 128/721 |
| 4,927,264 | 5/1990 | Shiga et al. | 356/41 |
| 4,945,916 | 8/1990 | Kretschmer et al. | 128/782 |
| 4,989,612 | 2/1991 | Fore | 128/721 |

FOREIGN PATENT DOCUMENTS

| | | | |
|---|---|---|---|
| 2034344 | 1/1972 | Fed. Rep. of Germany | 250/901 |
| 3737846 | 5/1989 | Fed. Rep. of Germany | 250/227.21 |

*Primary Examiner*—F. L. Evans
*Attorney, Agent, or Firm*—Benjamin J. Barish

[57] ABSTRACT

A device for detecting displacement of an object, particularly a chest belt for detecting respiration, includes an optical fibre having a light source at one end and a light-emitting face at the opposite end, a reflector device adjacent to and partially overlapping the light-emitting face of the optical fibre and movable with respect thereto to increase or decrease the amount of overlapping, a coupling for coupling the reflecting device to the object whose displacement is being detected, and a light sensor for sensing the amount of light reflected by the reflector back to the light-emitting face of the optical fibre and for outputting an electrical signal corresponding thereto.

7 Claims, 2 Drawing Sheets

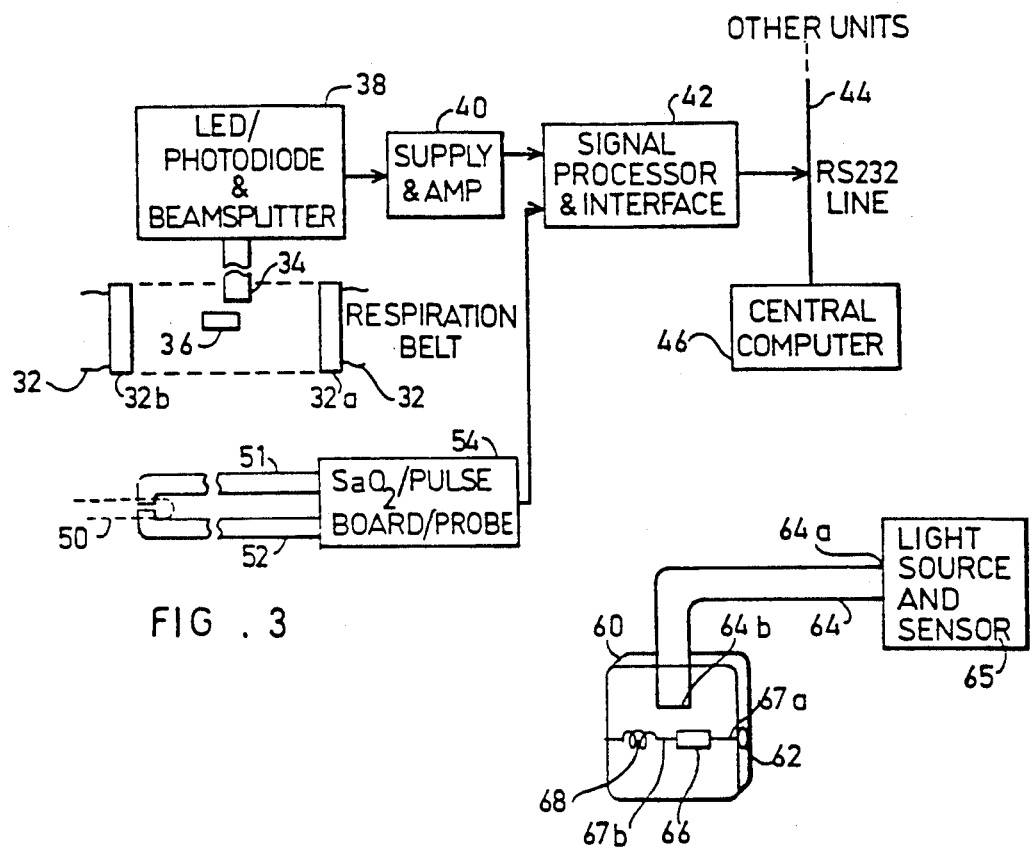
FIG. 3
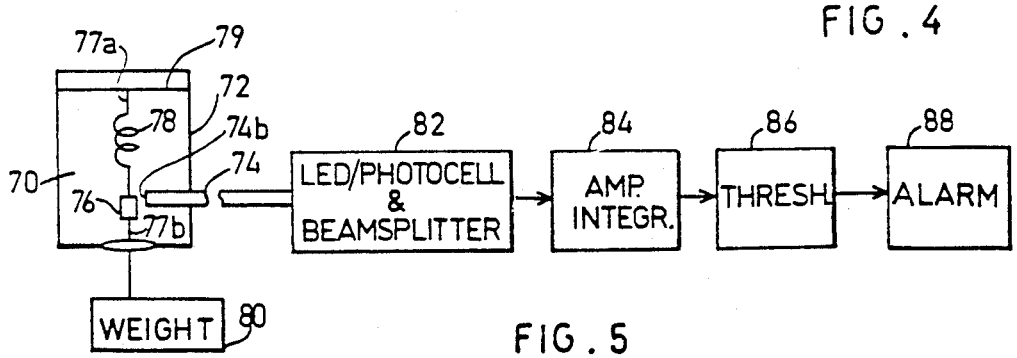
FIG. 4
FIG. 5
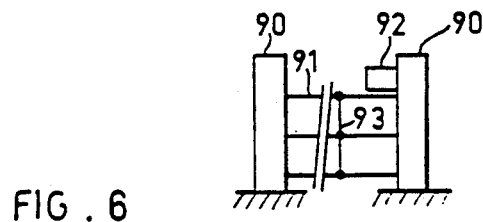
FIG. 6

DISPLACEMENT DETECTOR DEVICE AND METHOD

FIELD AND BACKGROUND OF THE INVENTION

The present invention relates to a device and also to a method for detecting displacement of an object. The displacement detected may be manifested in a number of forms, including movement, elongation (e.g., caused by a stress or change in temperature), deformation (e.g., of a diaphragm), and vibration. The invention is particularly useful in medical applications, e.g., for detecting respiration or pulse-rate but may also be used in a wide variety of non-medical applications, some of which are described below for purposes of example.

With respect to medical applications, several problems are present when monitoring vital signs of anesthetized patients, particularly infants and children unable to keep still during MRI (magnetic resonance imaging) procedures. Thus, when metallic electrodes and wires are used for this purpose, the metal in the electrodes and wires interfere with the image quality. In addition, the strong pulsating fields produced during the MRI procedure generate undesirable noise signals which interfere with the ECG and respiration monitors.

OBJECTS AND BRIEF SUMMARY OF THE INVENTION

An object of the present invention is to provide a displacement detector, and also a method of detecting and measuring displacements, which do not require wires or other metal parts at the detection site, and which thereby make the detector and method particularly useful in the above-mentioned medical applications, as well as in wide variety of other applications.

According to the present invention, there is provided a chest belt for detecting respiration, comprising: a buckle having first and second parts relatively movable with respect to each other along an axis of movement; a spring yieldable retaining the two buckle parts in an initial position; one of the buckle parts carrying an optical fibre having a planar light-emitting face oriented parallel the axis of movement of the two buckle parts; the other of the buckle parts carrying a mirror having a planar reflecting surface adjacent to, parallel to, and partially overlapping the light-emitting face of the optical fibre in the initial position of the two buckle parts; a light source for introducing light into the optical fibre; and a light sensor for sensing the light reflected by the reflecting surface of the mirror back to the light-emitting face of the optical fibre and for outputting an electrical signal corresponding thereto.

It will thus be seen that a displacement detector constructed in accordance with the foregoing features detects displacement optically, rather than electrically. Such a detector therefore obviates the need for electrical wires or other metal parts at the detector site or in the coupling from the detector site to the remotely-located processing system. The absence of electrodes, wires, or other metal parts at the detection site removes the possibility of such metal parts interfering with the image quality in an MRI procedure; it further prevents the pulsating fields used in such procedures from generating electrical noise signals which may interfere with the ECG, respiration, or other electrical monitors used during such procedures.

The electrical signal outputted by the light sensor may be interpreted in an analog fashion, or may be processed in accordance with the configuration of the light-emitting face of the optical fibre (whose dimensions would be known) to produce a measurement signal bearing a substantially linear relationship to the displacement detected.

Another major advantage, as compared for example with piezoelectric detectors, is that the outputted electrical signal follows the displacement substantially down to a steady state condition. Also, the detector requires much simpler circuitry.

While the invention is particularly useful in such medical applications, the invention may also be used in a wide variety of other applications, some of which are described below for purposes of example. Thus, the invention may also be used in a microphone to output electrical signals modulated according to sounds picked up by the microphone, a float for monitoring disturbances in the water containing the float, and a security fence for monitoring displacements or disturbances of the fence. Many other possible applications of the invention are also briefly mentioned below.

BRIEF DESCRIPTION OF THE DRAWINGS

The invention is herein described, by way of example only, with reference to the accompanying drawings, wherein:

FIG. 3 illustrates the device of FIG. 1 implemented in a vital-sign monitoring system for monitoring respiration, pulse rate and/or oxygen saturation of a patient;

FIG. 4 illustrates the device of FIG. 1 implemented in a microphone for outputting electrical signals modulated according to the sounds picked up by the microphone;

FIG. 5 illustrates the device of FIG. 1 implemented in a float detector for detecting disturbances in the water, e.g., of a swimming pool; and FIG. 6 illustrates the device of FIG. 1 implemented in a security fence for monitoring the displacement or disturbance of sensor wires in the fence.

DESCRIPTION OF PREFERRED EMBODIMENTS

Figure 1:
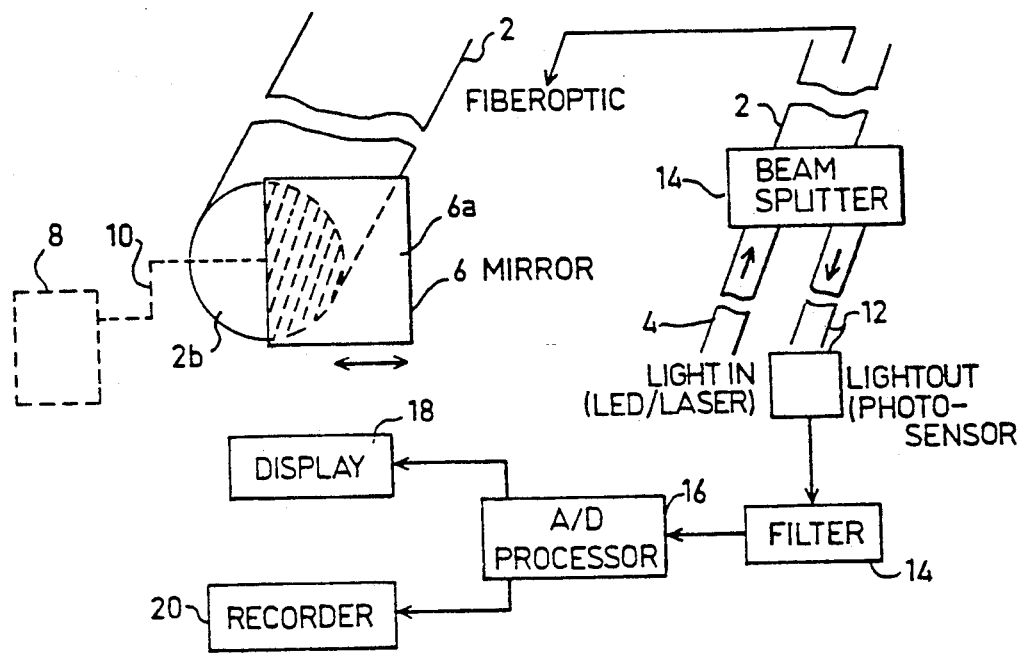
FIG. 1 illustrates one form of device constructed in accordance with the invention.

With reference to FIG. 1, there is illustrated one form of detector for detecting and measuring displacements of an object. As indicated earlier, such displacements may be the physical movement of the object, the elongation of the object (e.g., resulting from stress or temperature change), the deformation of the object (e.g., a diaphragm), the vibration of the object, etc. The displacement is detected purely by optical means, obviating the need for metal electrodes, wires or other metal elements, and the detector displacement is transmitted via purely optical means to a sensor which converts the optically-detected displacments to electrical signals. The sensor may be located at a remote site such that its metal parts or its electrical wires will not interfere with the equipment at the detection site (e.g., with the image quality in an MRI procedure) or will not be deleteriously affected by the medical (e.g., MRI) procedure.

The detector illustrated in FIG. 1 comprises an optical fibre 2 having a light source 4 at one end 2a, and a reflecting device or mirror 6 at the opposite end. The latter end of optical fibre 2 is formed with a planar light-emitting face 2b extending substantially perpendicularly to the longitudinal axis of the optical fibre 2. Mirror 6 is formed with a planar reflecting surface 6a which is located adjacent to and partially overlaps the light-emitting face 2b of the optical fibre 2 and is movable with respect to face 2b parallel to its planar surface to increase or decrease the amount of overlapping. Mirror 6 is mechanically coupled to the object, shown schematically at 8, whose displacement is to be detected and measured, by a mechanical coupling, shown schematically by broken line 10 so as to vary the amount of overlapping of reflecting surface 6a with respect to the light-emitting face 2b of the optical fibre in accordance with the displacement of the object 8.

The illustrated device further includes a light sensor 12 sensing the amount of light reflected by the reflecting surface 6a of mirror 6 back to the light-emitting face 2b of the optical fibre 2 and for outputting an electrical signal corresponding to the amount of light reflected back. Both the light source 4 and the light sensor 12 communicate with face 2b of the optical fibre 2 via a beam splitter 14, which permits the light from source 4 to be transmitted to face 2b of the optical fibre, and also permits the light reflected back through the optical fibre to be received by light sensor 12. In the initial position of mirror 6, its reflecting surface 6a overlaps exactly fifty percent of the light-emitting face 2b of the optical fibre 2. Accordingly, displacement of mirror 6 in one direction will produce an output signal of one sign, and displacing it in the opposite direction will produce an output signal of the other sign.

It will thus be seen that the system acts as a single fibre transponder sharing transmitted and received light, and that light sensor 12 will output electrical signals whose intensity is modulated in accordance with the change in the intensity of the light reflected back by mirror 6. These electrical signals are filtered by a band-pass filter 14 passing only the frequency band corresponding to the frequency of displacement of the object 8. For example, if the device is used for monitoring respiration, filter 14 would pass frequencies within the respiration frequency band, approximately 0.1-2 Hz; and if the detector is used for monitoring pulse rate, it would pass the pulse rate band frequency; approximately 2-15 Hz.

The output from filter 14 is fed to a processor 16 which processes this information as may be desired for any particular application. For example, the processor 16 may convert the analog output signals to digital form so as to enable processing it digitally. It may also process the outputted signals in accordance with known configurations and dimensions of the light-emitting face 2b of the optical fibre 2 to produce a measurement bearing a substantially linear relationship to the displacement detected.

Linearization may be effected not only by software, but also by a specially shaped opening in a light shutter or by mirror shaping.

The signals outputted from processor 16 thus provide a measurement of the displacement of object 8. Such measurements may be displayed in a display 18, recorded in a recorder 20, or processed further, in accordance with any particular application.

Figure 2:
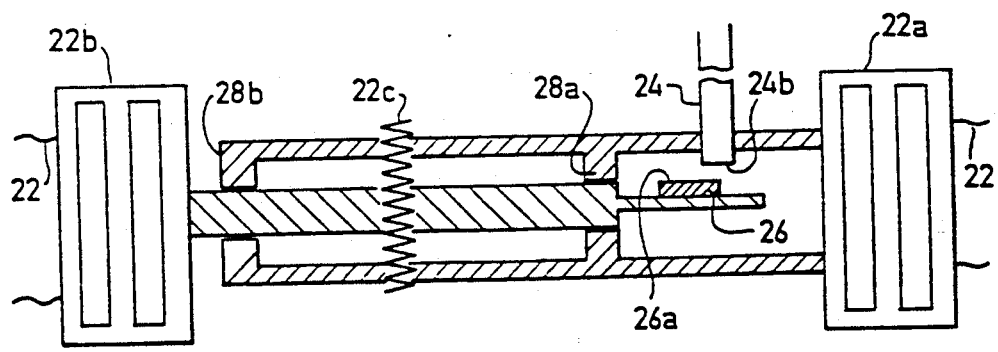
FIG. 2 illustrates the device of FIG. 1 implemented in a respiration detector for monitoring the respiration of a subject.

FIG. 2 illustrates the detector of FIG. 1 used in a chest belt to monitor respiration of a patient, e.g., a patient undergoing an MRI procedure. In this application, the chest belt 22 includes a buckle having two relatively-movable parts 22a, 22b connected together by a spring 22c which yieldably retains the two parts in the initial position. Buckle part 22a of the chest belt 22 carries the light-emitting face 24b of an optical fibre 24; and buckle part 22b carries the mirror 26 with its reflecting surface 26a adjacent and partially overlapping the light-emitting face 24b of the optical fibre. Light-emitting face 24b of the optical fibre 24 is planar and is parallel to the axis of movement of the two buckle parts 22a, 22b; and reflecting surface 26a is similarly planar, is adjacent to and partially overlaps the light-emitting face 24b. Spring 22c normally locates reflecting face 26a in an initial position overlapping one-half the light-emitting face 24b of the optical fibre. Guides 28a, 28b constrain the movement of mirror 26 substantially parallel to the plane of its reflecting face 26a and the plane of the light-emitting face 24b of the optical fibre.

It will thus be seen that when belt 22 is applied over the chest of a patient, the respiration of the patient will effect relative movement between reflecting face 26a of the mirror 26 with respect to the light-emitting face 24b of the optical fibre 24, so that the light reflected back by mirror 26 into the optical fibre will be modulated according to these movements. The so-modulated light is transmitted via optical fibre 2 to its opposite end, as illustrated in FIG. 1, wherein it is detected by the light sensor 12 outputting electrical signals corresponding to the detected displacements. Since the light sensor 12 may be located outside of the region of the medical procedure (e.g., MRI procedure) being performed on the patient, its electrical wires or other metal elements will not interfere with the medical procedure (i.e., image quality of the MRI) or be deleteriously affected by such procedure.

FIG. 3 illustrates a vital-sign monitoring system including the respiration monitoring device described above with respect to FIG. 2, and a pulse-rate and/or oxygen-saturation detector. The respiration detector in the system of FIG. 1 also includes a chest belt 32 provided with the two relatively-movable buckle parts 32a, 32b, part 32a carrying the optical fibre 34, and part 32b carrying the reflecting device 36, as described above with respect to FIG. 2. The output from optical fibre 34 is in the form of light modulated according to the detected chest displacements of the patient. The light output is fed to a light source (e.g., an LED), a photodiode and beam splitter, outputting electrical signals to an amplifier 40, which signals are processed by a processor 42 before being fed to a communciation bus 44 connected to a central computer 46.

For monitoring pulse-rate and/or oxygen saturation, the illustrated system further includes a clip 50 attachable to the ear lobe or finger of the respective patient for supporting a further pair of optical fibres 51, 52 having ends straddling the opposite sides of the ear lobe or finger tip so as to detect changes in light passing therethrough caused by the pulses or oxygen-saturation of the patient. The light signals are outputted from optical fibres 51, 52 to an oxygen saturation unit 54 (of known design) which converts the optically-sensed pulse rate and/or oxygen saturation to electrical signals. These are fed to the signal processor 42 for transmission via communication bus 44 to the central computer 46.

The system illustrated in FIG. 3 may thus be used for simultaneously monitoring vital signs of a large number of patients each wearing a chest belt 32 and an ear lobe or finger tip clip 50. The above vital signs of the respective patient are optically monitored and electrically fed to a central computer 46. Since both types of detectors at the monitoring site do not include any electrodes, electrical wires or other metal parts, they are relatively immune to power line, MRI, electro-surgical, and other possible interferences.

The invention is thus particularly useful with respect to the above-described medical applications, but it will be appreciated that the invention could also be advantageously used in many other applications. Some of these are illustrated for purposes of example in FIGS. 4–6.

FIG. 4 illustrates the device used as a microphone, generally designated 60, for outputting electrical signals modulated according to the sounds picked up by the microphone. Thus, the microphone 60 includes a membrane 62 which directly picks up the sounds, or is itself coupled to another device which picks up the sounds, the membrane being deformed according to the picked up sounds. An optical fibre 64 is mounted within microphone 60 with its outer face 64a coupled to a unit 65 including a light source and a light sensor (corresponding to elements 4, 12 and 14 in FIG. 1). The inner face 64b of the optical fibre is located within the microphone adjacent to a reflecting device (mirror) 66. Reflecting device 66 is coupled to membrane 62 by a first connection 67a, and to a fixed part of the microphone 60 by second connection 67b. The latter connection includes a spring 68 normally retaining reflecting device 66 in its initial position, i.e., overlapping fifty percent of the surface of the light-emitting face 64b of the optical fibre 64.

Accordingly, as membrane 62 is vibrated in response to the sounds picked up by the microphone 60, these vibrations will displace reflecting device 66 with respect to face 64b of optical fibre 64, to thereby modulate the light received by the sensor within unit 65, as described above with respect to FIG. 1, such that unit 65 will output electrical signals modulated according to the sounds picked up by membrane 62.

FIG. 5 illustrates the invention embodied in a water disturbance detector, such as may be used in a swimming pool, to produce an output signal or alarm should an object (e.g., person) enter the water. The water-disturbance detector illustrated in FIG. 5 is similar in construction to the microphone illustrated in FIG. 4. It includes a housing 70 closed at one end by a membrane 72 and receiving an optical fibre 74 facing a reflecting device 76 secured between membrane 72 and housing 70 by a first connection 77a and a second connection 77b, the latter including a spring 78. In this case, membrane 72 is connected to a float 79, and the housing 70 includes a weight 80, both so designed such that the float retains housing 70 in a stable submerged condition in the absence of water waves. In this stable condition, reflecting device 76 is located so as to overlie fifty percent of the light-emitting surface 74b of the optical fibre 74.

However, whenever an object enters the water, waves will be created. These will move float 79 with respect to housing 70, thereby causing membrane 72 to be displaced and to move reflecting device 76 with respect to the light-emitting face 74b of the optical fibre 74. The modulation in the light by these displacements of reflecting device 76 are converted to electrical signals in unit 82, filtered and amplified in unit 84, and passed through a threshold detector 86, which determines whether the disturbances are sufficient to actuate an alarm 88.

It will be appreciated that instead of suspending housing 70 by weight 80, the housing may be attached to the side of the swimming pool or to another object fixed to the side of the swimming pool.

FIG. 6 illustrates a security fence equipped with a displacement or disturbance detector in accordance with the invention. Thus, the security fence illustrated in FIG. 6 includes a plurality of stakes 90 anchored in the ground and supporting a plurality of fence wires 91 in tension. The displacement detector, generally designated 92, may be of the same construction as described above with respect to FIGS. 1, 4 or 5, to include an optical fibre and a reflecting device relatively displaceable with respect to each other whenever one of the fence wires 91 is displaced. For example, the optical fibre (corresponding to 2 in FIG. 1) may be secured to the fence post 90, and the reflecting device (corresponding to 6 in FIG. 1), may be secured to one or more of the fence wires 91, or vice versa. All the fence wires 91 may be coupled together by a common coupling wire 93, such that the displacement, or any disturbance, of one of the fence wires 91 will be transmitted to the displacement detector 92 which will output an electrical signal corresponding to the displacement detected.

The displacement detector 92 may be coupled to a light transmitter/receiver unit corresponding to unit 82 in FIG. 5, and may also include the filter/amplifier unit, threshold detector and alarm corresponding to units 84, 86 and 88 in FIG. 5.

While the invention has been described with respect to several preferred applications, many other applications will be apparent. For example, the detector may be used as a low-cost replacement of an LVDT (linear variable differential transformer) for small displacements and as a stain gauge. Unlike piezoelectric material, its DC response allows a low cost weight sensor to be produced with remote electronics. The detector may also be used for detecting other forms of displacements, e.g., vibration in an engine, eye movements during sleep, earth tremors in seismometry, elongation caused by stresses or heat, intrusion (e.g., door mats), tactile switches, acoustic sensors, wind measurement sensors, shock wave and impact sensors, force transducers, level and position sensors, crib mattress apnea monitors, remote control switches for the handicapped, tennis net and foul line remote impact sensors, etc.

It will therefore be appreciated that the embodiments described herein are set forth purely for purposes of example, and that many other variations, modifications and applications of the invention may be made.

What is claimed is:

1. A chest belt for detecting respiration, comprising:
   a buckle having first and second parts relatively movable with respect to each other along an axis of movement;
   a spring yieldable retaining the two buckle parts in an initial position;
   one of said buckle parts carrying an optical fibre having a planar light-emitting face oriented parallel to the axis of movement of the two buckle parts;
   the other of said buckle parts carrying a mirror having a planar reflecting surface adjacent to, parallel to, and partially overlapping said light-emitting face of the optical fibre in said initial position of the two buckle parts;
   a light source for introducing light into said optical fibre;

and a light sensor for sensing the light reflected by said reflecting surface of the mirror back to the light-emitting face of the optical fibre and for outputting an electrical signal corresponding thereto.

2. The chest belt according to claim 1, wherein one of said buckle parts includes guiding means for constraining the movement of the other buckle part to said axis of movement.

3. The chest belt according to claim 2, wherein said first buckle part carrying said optical fibre includes said guiding means for constraining the movement of said second buckle part, carrying said mirror, to said axis of movement.

4. The chest belt according to claim 1, further including a beam splitter at one end of said optical fibre for transmitting light from said light source into the optical fibre, and for transmitting to said sensor the light reflected back through the optical fibre by said reflector surface.

5. The chest belt according to claim 1, further including a bandpass filter receiving said outputted electrical signal and effective to pass only the frequency band thereof corresponding to the frequency of respiration to be detected.

6. The chest belt according to claim 1, further including a processor for processing said outputted electrical signal from the light sensor to produce output signals corresponding to the detected respiration.

7. The chest belt according to claim 6, further including optical fibre means carried by a clip attachable to a part of patient's body and coupled to said processor for detecting pulse rate and/or oxygen saturation in addition to respiration.

* * * * *